United States Patent
Mestroni et al.

(12)

(10) Patent No.: US 6,921,824 B1
(45) Date of Patent: Jul. 26, 2005

(54) RUTHENIUM DIMERIC COMPLEXES SUITABLE AS ANTIMETASTATIC AND ANTINEOPLASTIC AGENTS

(75) Inventors: Giovanni Mestroni, Trieste (IT); Enzo Alessio, Trieste (IT); Gianni Sava, Trieste (IT); Elisabetta Iengo, Trieste (IT); Sonia Zorzet, San Canzian Isonzo-Pieris (IT); Alberta Bergamo, Trieste (IT)

(73) Assignee: SIGEA S.r.l., Trieste (IT)

( * ) Notice: Subject to any disclaimer, the term of this patent is extended or adjusted under 35 U.S.C. 154(b) by 0 days.

(21) Appl. No.: 09/958,759
(22) PCT Filed: Apr. 18, 2000
(86) PCT No.: PCT/EP00/03484

§ 371 (c)(1),
(2), (4) Date: Oct. 15, 2001

(87) PCT Pub. No.: WO00/63218

PCT Pub. Date: Oct. 26, 2000

(30) Foreign Application Priority Data

Apr. 19, 1999 (IT) .......................................... MI99A0811

(51) Int. Cl.[7] .......................... C07B 279/00; C07D 9/80; C07D 205/00; C07F 15/00

(52) U.S. Cl. .............................. 544/4; 546/3; 540/201; 540/541; 548/103; 548/105
(58) Field of Search ................... 544/4; 546/3; 540/201, 540/541; 548/103, 105

(56) References Cited

FOREIGN PATENT DOCUMENTS

WO    WO 98/00431    1/1998

OTHER PUBLICATIONS

Creutz, C. et al, Binuclear complexes of Ruthenium Ammines, *Journal of American Chemical Society*, pp. 1086–1094, Feb. 1973.

Keppler, B.K. et al, Antitumor activity of imidazolium–bi-simidazole–tetrachlororuthenate (III) *J. Cancer Research Clin Oncology*, vol. 111, pp. 166–168, 1986.

*Primary Examiner*—Cecilia J. Tsang
*Assistant Examiner*—Raymond Covington
(74) *Attorney, Agent, or Firm*—William S. Feiler; Morgan & Finnegan, L.L.P.

(57) ABSTRACT

New ruthenium dimeric complexes with high antimetastatic and antitumour activity and remarkable chemical stability are described.

23 Claims, 1 Drawing Sheet

RUTHENIUM DIMERIC COMPLEXES SUITABLE AS ANTIMETASTATIC AND ANTINEOPLASTIC AGENTS

FIELD OF THE INVENTION

The present invention relates to antitumour compounds, particularly endowed with antimetastatic activity.

PRIOR ART

Several ruthenium-based compounds are described in the literature also in relation to their activity on several types of tumour both in vitro and in vivo.

Several anionic ruthenium (III) complexes have been tested for their antitumour activity; among them, for example ImH[trans-RuCl$_4$Im$_2$], (B. K. Keppler et al., J. Cancer Res. Clin. Oncol., 111: 166–168, 1986) and complexes of the type Na[trans-RuCl$_4$(Me$_2$(SO)(L)], (L=nitrogen-containing ligand) (WO90/13553) which have been proved effective in particular in slowing down the growth of the primary tumour.

More recently, studies carried out on complexes of the type (LH)[trans-RuCl$_4$(Me$_2$SO)(L)] (WO 90/00431) have shown that the anionic compounds of this class have a remarkably selective antimetastatic activity. In particular, this study was relevant in the field of compounds with antimetastatic activity, i.e. compounds able to selectively interfere with the formation of metastases, but with very marginal or no effects on the primary tumour.

The search for new antineoplastic agents keeps on developing, being mainly devoted to the identification of new compounds with high selectivity, reduced toxic effects, or active on tumours not responsive to classical antitumor treatment. In this framework, antimetastatic drugs are extremely important since it is known that the metastases of solid tumour are the main cause for failure of the medical treatment and spreading of the tumor. Current medical treatments are based on drugs mainly studied for their activity on the primary tumour, not on metastases. It is worth remembering that metastasis have a biological behaviour which is quite different from the primary tumours: in metastatic cells the antigenic features and the regulation of the cell cycle are quite different from those of the solid tumour. Furthermore, the response to cytotoxic agents is not identical in the two cases and the selection of new antimetastatic agents requires studies aimed at targeting the specific problem of the dissemination of the metastatizing solid tumour cells. Several ruthenium dimeric complexes are known, characterised in their structures by the presence of nitrogen-containing bridging ligands belonging to the categories of: di-nitrogen heterocycles, pyridine rings linked one another either directly or by means of saturated and unsaturated aliphatic chains. In all cases they can be classified as cationic ruthenium dimers. They have been extensively studied from the viewpoint of their electrochemical and photophysical properties (Creutz et al., Journal Am. Chem. Soc. 1973, 21, 1086).

SUMMARY OF THE INVENTION

New ruthenium dimeric complexes, either anionic or neutral, either symmetrical or asymmetrical, are herein described. The two ruthenium atoms of said complexes have an oxidation state (III) and are bound by means of a nitrogen heterocyclic ligand containing at least two nitrogen heteroatoms. Said nitrogen heteroatoms are further bound with substituents selected between: Cl$^-$, OS(R$_1$R$_2$). The complexes object of the present invention show a remarkable chemical stability and a high antimetastatic activity. They can be used in the prevention and therapy of tumour, especially those with an elevated degree of metastatic diffusion, such as the digestive tract carcinomas, mammary carcinomas, and lung carcinomas.

DESCRIPTION OF THE FIGURES

FIG. 1a

Decrease of the absorbance percentage in H$_2$O at T=25° C. for:
[Na]$_2$[trans-RuCl$_4$(Me$_2$SO)]$_2$($\mu$-pyz)(es.4): □
[Na]$_2$[trans-RuCl$_4$(Me$_2$SO)]$_2$($\mu$-pym)(es.7): ○
[Na]$_2$[trans-RuCl$_4$(Me$_2$SO)]$_2$($\mu$-4,4'-bipy)(es.8): ▲
[Na]$_2$[trans-RuCl$_4$(Me$_2$SO)]$_2$($\mu$-etbipy)(es.10): ♦
[trans-RuCl$_4$(Me$_2$SO)(Im)][ImH]: +

FIG. 1b

Decrease of the absorbance percentage in physiological buffer at T=25° C. for:
[Na]$_2$[trans-RuCl$_4$(Me$_2$SO)]$_2$($\mu$-pyz)(es.4): □
[Na]$_2$[trans-RuCl$_4$(Me$_2$SO)]$_2$($\mu$-pym)(es.7):
[Na]$_2$[trans-RuCl$_4$(Me$_2$SO)]$_2$($\mu$-4,4'-bipy)(es.8): ○
[Na]$_2$[trans-RuCl$_4$(Me$_2$SO)]$_2$($\mu$-etbipy)(es.10): ▲
[trans-RuCl$_4$(Me$_2$SO)(Im)][ImH]: +

DETAILED DESCRIPTION OF THE INVENTION

The compounds object of the present invention are ruthenium dimeric complexes belonging to the class of antineoplastic agents.

We have found that the simultaneous presence of two ruthenium nuclei associated to structural groups different from those already described produces derivatives with a considerable antitumour activity, in particular antimetastatic. This activity is associated with a remarkable chemical stability which makes these products extremely suitable for pharmaceutical formulation.

The complexes object of the present invention have the following general formula (I):

wherein L represents an heterocyclic ligand containing at least two nitrogen heteroatoms, wherein the electronic doublets of said nitrogen atoms are involved in the bond with two ruthenium atoms;

X,Y and Z, independent from one another, represent: Cl$^-$, —OS(R$_1$R$_2$);

R$_1$ and R$_2$ either represent, independent from one another C$_1$–C$_6$ alkyl, C$_3$–C$_7$ cycloalkyl, phenyl and aryl or R$_1$ and R$_2$, together with the sulfur atom, form a heterocyclic ring with 5–7 membered heterocyclic ring;

m is an integer ranging from 0 to 2;

when m is different from 0, the negative charge of the compound of formula (I) is neutralized by a counterion Q which is suitable for pharmaceutical use.

The heterocyclic ligand L corresponding to formula (I) always contains two nitrogen atoms bound by means of their electronic doublets to the two ruthenium atoms of formula (I). Said nitrogen atoms can be present either in the same heterocyclic ring, as for example in pyrazine or pyrimidine, or in two separate heterocyclic rings. In this case, the L ligand takes the A'—K—A" structure wherein A' and A" represent the two nitrogen heterocycles that are bonded to two ruthenium atoms and K preferably represents: —COO—, —O—, —(CH$_2$)$_n$—, —(CH=CH)$_n$—, -(aryl)$_n$-, -(heterocycle)$_n$-, —CH=CH—Phe—CH=CH—, —(C≡C)$_n$, where n ranges from 0 to 4.

The heteroaromatic rings and the optional aromatic rings contained in the A'—K—A" structure, can be either fused or not and substituted with alkyl groups having from 1 to 6 carbon atoms (where methyl and ethyl groups are preferred), $C_1$–$C_4$ alkoxy, phenyl, CN, $NO_2$.

Examples of not fused heteroaromatic rings are: pyrrole, imidazole, pyrazole, pyrazine, pyrimidine, pyridine.

Examples of fused heteroaromatic rings are: quinoline, isoquinoline, carbazole.

Examples of fused aromatic rings are: naphtalene, anthracene, phenantrene.

Preferred examples of ligands with A'—K—A" structure, the structure of which is illustrated hereunder, are:
4,4'-bipyridil: (A=A"=pyridine, K=—(CH$_2$)$_n$—, wherein n=0),
bis-imidazole: (A=A"=imidazole, K=—(CH$_2$)$_n$—, wherein n=0),
1,2-bis(4-pyridil)ethane: (A=A"=pyridine, K=—(CH$_2$)$_n$—, wherein n=2),
1,2-bis(4-pyridil)propane: (A=A"=pyridine, K=—(CH$_2$)$_n$—, wherein n=3),
trans-1,2-bis(4-pyridil)ethylene: (A=A"=pyridine, K=—(CH=CH)$_n$—, wherein n=1)

4,4'-bipyridil
(4,4'-bipy)

1,2-bis(4-pyridil)ethane
(etbipy)

1,2-bis(4-pyridil)propane
(prbipy)

trans-1,2-bis(4-pyridil)ethylene
(etilbipy)

As far as the $R_1$ and $R_2$ substituents are concerned, the —OS($R_1R_2$) group is preferably represented by dimethyl-sulfoxide ($R_1=R_2$=methyl), diethylsulfoxide ($R_1=R_2$=ethyl) or tetramethylensulfoxide ($R_1$ and $R_2$ together with the S atom form a 5-membered ring).

When present, the Q counterion is preferably selected in the group consisting of a cation of alkaline metals or alkaline earth metals, or a cation having the formula $NHR_3R_4R_5^+$ wherein $R_3,R_4$, $R_5$, either identical or different, can be H, $C_1$–$C_6$ alkyl, $C_3$–$C_7$ cycloalkyl, phenyl and aryl, or $NHR_3R_4R_5^+$ is a nitrogen-containing 5–7-membered heterocycle optionally fused with a benzyl group. Preferred examples of Q are $Na^+$, $K^+$, $NH_4^+$, $NEt_4^+$(ethyl-ammonium), $ImH^+$(imidazolium).

The two ruthenium nuclei, linked by the L heterocyclic ligand, are in the oxidation state (III). The two Ru(III) nuclei can have either the same (symmetric dimers) or different (asymmetrical dimers) coordination groups.

The compounds represented by formula (I) can be either anionic or neutral according to the nature of the L ligands; the negative charges of anions are neutralized by a corresponding number of Q cations.

By varying X and Y in formula (I), dimers belonging to the following three groups are obtained and represented hereunder by the (Ia)–(Ic) formulas, all included in the general formula (I).
(Ia): dianionic symmetric Ru (III) dimers: X=Y=Z=Cl$^-$
(Ib): asymmetric mono-anionic Ru(III) dimers: X=Z=Cl$^-$; Y=OSR$_1$R$_2$
(IC): symmmetric neutral dimers of Ru(III): X=Y=OSR$_1$R$_2$; Z=Cl$^-$ A further object of the present invention is the process for the preparation of formula (I) complexes, in particular processes for the preparation of formula (Ia)–(Ic) compounds.

All these processes include a step where a precursor of formula (III), where W represents: Cl⁻, —OS(R₁R₂) and $R_1$, $R_2$ and m maintain the same meaning as above, is reacted with the L ligand as defined above in the presence of an organic solvent and in adequate molar ratios.

As far as (Ib) asymmetric ruthenium complexes are concerned, the process comprises the isolation of an intermediate compound obtained from the reaction between the formula (III) precursor and the L ligand. In a second step, the intermediate is reacted with another formula (III) precursor, wherein the meaning chosen for W is different from that selected for the first precursor.

The different processes to obtain the ruthenium compounds having (Ia–Ic) formula are hereinafter specifically described.

Preparation of Dianonic Ru(III) Dimers of Formula (Ia)

The symmetric dianionic dimeric compounds of formula (Ia) are obtained in a single step starting from the Ru(III) precursor of formula: Q[trans-RuCl₄(R₁R₂SO)₂] (Q⁺=Na⁺, K⁺, NH₄⁺) which is reacted at room temperature with the L ligand preferably in a 1:0.5 molar ratio, in organic solvents or their mixtures, preferably acetone, methanol or acetone/dimethylsulfoxide mixtures, according to the general scheme reported hereunder:

At this stage, two molecules of the precursor react with one molecule of the L ligand allowing the substitution of one of the two axial sulfoxide groups in each precursor molecule and the obtainment of (Ia) complexes at high yields.

Preparation of Asymmetric Monoanionic Ru(III) Dimers of Formula (Ib).

The asymmetric monoanionic Ru(III) dimers of formula (Ib) are obtained in two steps: the first allows the monocoordination of the ligand to a Ru(III) precursor (either anionic or neutral) of formula (III); the product is isolated and further reacted with the complementary precursor (respectively neutral or anionic) to get to the final product. The reaction is therefore carried out according to the two possible ways indicated in the following scheme:

The preferred reaction route to obtain complexes according to the invention is the following:

Step 1): reaction of the known Ru(III) precursor the having formula [mer-RuCl₃(Me₂SO)₃] ($R_1=R_2=CH_3$) with the L ligand in molar ratios ranging preferably from 1:2 to 1:6, in one or more organic solvents, preferably acetone or chloroform, according to the scheme reported hereunder:

During this step, the precursor reacts with a molecule of the ligand L leading to the substitution of one or two axial sulfoxide groups to obtain monomeric complexes (II) at high yields. In these complexes one or two basic groups of the ligand L are still available for further coordination.

Step 2) reaction of the monomeric complex of formula (II) with the anionic Ru(III) precursor of formula Q[trans-RuCl$_4$(R$_1$R$_2$SO)$_2$] in molar ratios ranging preferably from 1:0.4 to 1:0.75, in one or more organic solvents, preferably nitromethane or methanol, according to the scheme hereunder reported:

Preparation of the Symmetric Neutral Ru(III) Dimers of Formula (Ic).

The symmetric neutral dimers of formula (Ic) are obtained in a single step starting from the known Ru(III) precursor of formula [mer-RuCl$_3$(Me$_2$SO)$_3$] which is reacted at room temperature with the ligand L preferably at 1:0.5 molar ratio, in one or more organic solvents, preferably acetone or chloroform, according to the scheme reported hereunder:

In this step, two molecules of the precursor are reacted with one molecule of the L ligand leading to the substitution of one or two axial sulfoxide groups in each molecule of the precursor and (Ic) complexes at high yields are obtained.

Surprisingly, the dimeric complexes of the present invention are markedly more stable in solution, both aqueous and physiological, than the ruthenium compounds already known in the state of the art. Because of their high stability it is possible to overcome the inconveniences related to the processing of labile products. This facilitates not only the administration but also the preparation of suitable pharmaceutical formulations with appropriate dosage and administration of the active form of the compound.

The complexes of the present invention can be profitably used in the treatment of various kind of neoplastic diseases.

The present invention therefore provides for the use of complexes of formula (I) in the preparation of drugs useful for the prevention and treatment of metastases and tumours. The compounds of the invention are particularly useful for the treatment of solid metastatizing tumours, such as the carcinomas of the digestive tract, mammary carcinomas, lung tumours, metastatic carcinomas and lung metastases of metastastic tumours.

The administration of the compounds of the present invention can be carried out either before or after the surgical removal of the primary tumour.

As shown in the experimental results reported in examples 15 and 16, the in vivo models related to the treatment of a metastatizing solid tumour, such as the MCa mammary carcinoma, with the compounds of the present invention, show a marked and statistically significant reduction in metastases formation. This reduction is observed either when the treatment is performed before surgical removal of the primary tumor or after it. These new complexes turn out to be very interesting both for their preventive activity on the formation of metastases and for their inhibitory activity on metastases at an advanced stage of growth. It is moreover interesting to note that these compounds have proved to be active on metastases at different dose levels.

The use of these complexes in the treatment of neoplasms can also be carried out within polychemotherapeutical treatment protocols. The compounds of the present invention therefore can be used in combination with other antitumoural drugs, such as for example cisplatin, 5-fluorouracyl, vinblastine, cyclophosphamide, bleomycin, anthracyclin, taxole, in the pathologies reported above.

The present invention further provides pharmaceutical compositions containing the complexes of formula (I) in combination with pharmaceutically acceptable excipients and diluents. In said compositions, the complex of formula (I) can also be present in combination with known antitumour and/or antimetastatic drugs, such as those exemplified above.

The pharmaceutical compositions object of the present invention can be prepared for the parenteral, oral, topical, and transdermal administration. The preferred routes of parenteral administration are the intravenous, intramuscular, intraperitoneal and subcutaneous routes.

When they are in a liquid form, the compositions of the present invention are in the form of a solution or suspension, both in aqueous and non-aqueous medium. Alternatively, they can be formulated as freeze-dried solid that can be solubilized or resuspended by addition of liquid medium just before administration.

When they are in a solid or semisolid form, the pharmaceutical compositions can be inserts, gel, cream, granules, powder, tablets, capsules, pills and so on.

The different compositions described above can be formulated so as to have a controlled delivery of the active compound.

All the preparations of the described formulations can be carried out according to the procedures already known in the state of the art.

For the illustrative but not limitative purposes of the present invention, the following examples of synthesis of the complexes and characterisation of their pharmacological activity are hereunder provided.

EXPERIMENTAL PART
Preparation of the Ruthenium Complexes According to the Invention

EXAMPLE 1

Preparation of [K][trans-RuCl$_4$(Me$_2$SO)$_2$]

This compound was prepared starting from the precursor [(Me$_2$SO)$_2$H][trans-RuCl$_4$(Me$_2$SO)$_2$] following a procedure identical to the one described for the corresponding sodium salt [Na][trans-RuCl$_4$(Me$_2$SO)$_2$](E. Alessio, G. Balducci, M. Calligaris, G. Costa, W. M. Attia, G. Mestroni *Inorg. Chem.* 1991, 30, 609) using KCl instead of NaCl.

The physico-chemical features of the product [K][trans-RuCl$_4$(Me$_2$SO)$_2$] were as follows:
Physical state: red-orange microcrystalline solid
Raw formula: C$_4$H$_{12}$Cl$_4$KO$_2$RuS$_2$
Molecular weight: 438.24
Elemental analysis:
Theoretical: C, 10.9; H, 2.76
Experimental: C, 10.8; H, 2.71

The spectra in solution (UV-vis, NMR) confirmed the presence of the anion [trans-RuCl$_4$(Me$_2$SO)$_2$]$^-$.

EXAMPLE 2

Preparation of [NH$_4$][trans-RuCl$_4$(Me$_2$SO)$_2$]

0.56 g of [(Me$_2$SO)$_2$H][trans-RuCl$_4$(Me$_2$SO)$_2$](1 mmole) was dissolved in 23 ml of ethanol and 0.3 ml of H$_2$O. 96 mg of NH$_4$Cl (1.8 mmoles) was dissolved in 0.3 ml of H$_2$O and was added under stirring to the first solution. The product precipitated soon as an abundant orange-coloured microcrystalline solid that was immediately filtered in vacuum, washed with cold acetone and ethyl ether and finally vacuum-dried. Yield: 0.3 g (75%).

The physico-chemical features of [NH$_4$][trans-RuCl$_4$(Me$_2$SO)$_2$] were as follows:
Physical state: orange microcrystalline solid
Raw formula: C$_4$H$_{16}$NCl$_4$O$_2$RuS$_2$
Molecular weight: 417.16
Elemental analysis:
Theoretical: C, 11.5; H, 3.87; N, 3.36
Experimental: C, 11.6; H, 3.78; N, 3.37

The spectra in solution (UV-vis, NMR) confirm the presence of the anion [trans-RuCl$_4$(Me$_2$SO)$_2$]$^-$.

EXAMPLE 3

Preparation of [ImH][trans-RuCl$_4$(Me$_2$SO)$_2$]

0.5 g of [(Me$_2$SO)$_2$H][trans-RuCl$_4$(Me$_2$SO)$_2$] (1 mmole) was dissolved in 23 ml ethanol+0.3 ml of H$_2$O. 188 mg of solid ImHCl (1.8 mmoles) was added under stirring. The product immediately precipitated in the form of an abundant red-orange microcrystalline solid which was immediately filtered in vacuum, washed with cold ethanol, cold acetone and ethyl ether and vacuum-dried. Yield: 0.35 g (75%).

The physico-chemical features of [(ImH][trans-RuCl$_4$(Me$_2$SO)$_2$] are as follows:
Physical state: red-orange microcrystalline solid
Raw formula: C$_7$H$_{17}$N$_2$Cl$_4$O$_2$RuS$_2$
Molecular weight: 468.22
Elemental analysis:
Theroretical: C, 17.9; H, 3.65; N, 5.98
Experimental: C, 18.1; H, 3.67; N, 5.94

The solution spectra (UV-vis, NMR) confirmed the presence of both the anion [trans-RuCl$_4$(Me$_2$SO)$_2$]$^-$ and the ImH$_+$ cation.

EXAMPLE 4

Preparation of [Na][trans-RuCl$_4$(Me$_2$SO)$_2$]($\mu$-pyz), Corresponding to Formula (Ia) with Q$^+$=Na$^+$, L= pyrazine (pyz) and R$_1$=R$_2$=methyl 0.200 g of Na[trans-RuCl$_4$(Me$_2$SO)$_2$] (47.4 mmoles) was dissolved in 2.5 ml of Me$_2$SO. A solution of 0.019 g of pyrazine (23.7 mmoles) in 5 ml of acetone was added to the system under stirring. Then, the turbid orange solution obtained was filtered over paper and the filter was washed with about 3 ml of acetone. The filtered solution was then kept at room temperature, for one night. The product precipitated as red microcrystals. Then it was filtered in vacuum, washed with cold acetone and ether and vacuum-dried. Yield: 0.20 g (83%).

The physico-chemical features of the product were as follows:
Physical state: red orange microcrystalline solid
Raw formula: C$_8$H$_{16}$N$_2$Cl$_8$Na$_2$O$_2$Ru$_2$S$_2$.0.3(Me$_2$SO).H$_2$O
Molecular weight: 1020.44
Elemental analysis:
Theoretical: C, 16.5; H, 3.56; N, 2.75
Experimental: C, 16.6; H, 3.52; N, 2.71
UV/Vis spectrum in H$_2$O ($\lambda_{max}$, nm): 470.5, 391
$^1$H-NMR spectrum in D$_2$O (ppm vs DSS): −14.3 (very broad, Me$_2$SO)
IR spectrum (selected frequencies, nujol, cm$^{-1}$): $\upsilon$ (S—O) 1074, vs; $\upsilon$ (Ru–S) 437, m; $\upsilon$ (Ru–Cl)330, s.

EXAMPLE 5

Preparation of [NH$_4$]$_2$[trans-RuCl$_4$(Me$_2$SO)]$_2$ ($\mu$-pyz), Corresponding to Formula (Ia) with Q$^+$= NH$_4^+$, L=pyrazine (pyz) and R$_1$=R$_2$=methyl 38 mg of [Na]$_2$[trans-RuCl$_4$(Me$_2$SO)]$_2$($\mu$-pyz) (0.037 mmoles) was dissolved in 2 ml of H$_2$O. An excess of NH$_4$Cl was added to the solution under stirring. A dark orange precipitate was formed and was then filtered in vacuum, washed with cold acetone and ether and vacuum-dried. Yield: 23 mg (80%). In agreement with elemental analysis, the compound contained one crystallization water molecule.

The physico-chemical features of the product were as follows:
Physical state: red-orange solid
Raw formula: C$_8$H$_{24}$N$_4$Cl$_8$O$_2$Ru$_2$S$_2$.H$_2$O
Molecular weight: 776.20
Elemental analysis:
Theoretical: C, 12.3; H, 3.37; N, 7.22
Experimental: C, 12.1; H, 3.38; N, 7.13
UV/vis Spectrum in H$_2$O ($\lambda_{max}$, nm): 470.5, 391
$^1$H-NMR in D$_2$O (ppm vs DDS): −14.3 (very broad, Me$_2$SO)

EXAMPLE 6

Preparation of [K]$_2$[trans-RuCl$_4$(Me$_2$SO)]$_2$($\mu$-pyz), Corresponding to Formula (Ia) with Q$^+$=K$^+$, L= Pyrazine (pyz) and R$_1$=R$_2$=Methyl 0.200 g of K[trans-RuCl$_4$(Me$_2$SO)$_2$] complex (46.0 mmoles) was partially dissolved in 10 ml acetone. 0.018 g of pyrazine (23.0 mmoles) were added to the mixture under stirring. The system was kept under stirring for four hours; the precipitate was then filtered in vacuum, washed with cold acetone and ethyl ether and vacuum-dried. Yield: 0.15 g (80%). (The compound was not very soluble in water). The physico-chemical features of [K]$_2$[trans-RuCl$_4$(Me$_2$SO)]$_2$ ($\mu$-pyz) are as follows:

Physical state: red-orange microcrystalline solid
Raw formula: $C_8H_{16}N_2Cl_8O_2Ru_2S_2K_2$
molecular weight: 800.07
Elemental analysis:
Theoretical: C, 12.0; H, 2.02; N, 3.52
Experimental: C, 12.0; H, 2.24; N, 3.24

The spectroscopic features of the product in solution were the same as those of the corresponding sodium salt.

EXAMPLE 7

Preparation of $[Na]_2[trans-RuCl_4(Me_2SO)]_2(\mu$-pym), Corresponding to Formula (Ia) with $Q^+=Na^+$, L=pyrimidine (pym) and $R_1=R_2$=methyl The synthesis was carried out as for the corresponding dimer with pyrazine. From 0.220 g of $[Na][trans-RuCl_4(Me_2SO)]_2$ (52.1 mmoles) in 2 ml of $Me_2SO$ and 0.021 g of pyrimidine (26.2 mmoles) in 5 ml of acetone, a red-orange microcrystalline product was obtained. Yield: 0.175 g (65.8%).

The physico-chemical features of $[Na]_2[trans-RuCl_4(Me_2SO)]_2$ ($\mu$-pym) were as follows:
Physical state: red-orange microcrystalline solid
Raw formula: $C_8H_{16}N_2Cl_8Na_2O_2Ru_2S_2 \cdot 3(Me_2SO) \cdot H_2O$
Molecular weight: 1020.44
Elemental analysis:
Theoretical: C, 16.5; H, 3.56; N, 2.75
Experimental: C, 16.6; H, 3.49; N, 2.69
UV/vis Spectrum in $H_2O$ ($\lambda_{max}$, nm): 470,402
$^1$H-NMR spectrum in $D_2O$ (ppm vs DSS): −14.25 (very broad, $Me_2SO$); −10 (broad, H5; pym-Ru)
IR Spectrum (selected frequencies, nujol, cm$^{-1}$): $\upsilon$ (S—O) 1081, vs; $\upsilon$ (Ru—S) 433, m; $\upsilon$ (Ru—Cl) 341, s.

EXAMPLE 7.bis

Preparation of $[ImH]_2[trans-RuCl_4(Me_2SO)]_2(\mu$-pym), Corresponding to Formula (Ia) with $Q^+=$ImH$^+$, L=pyrimidine (pym) and $R_1=R_2$-methyl 51 mg of the $[Na]_2[trans-RuCl_4(Me_2SO)]_2(\mu$-pym) (0.05 mmoles) complex was dissolved in 9 ml of methanol. 42 mg (0.4 mmoles) of ImHCl was added to the solution which was kept under stirring. An orange precipitate was obtained which was filtered in vacuum, washed with methanol and ether and vacuum-dried. Yield: 35 mg (80%).

The physicochemical features of $[ImH]_2[trans-RuCl_4(Me_2SO)]_2(\mu$-pym) were as follows:
Physical state: orange microcrystalline solid
Raw formula: $C_{14}H_{26}N_6Cl_8O_2Ru_2S_2$
Molecular weight: 860.28
Elemental analysis:
Theoretical: C, 19.5; H, 3.00; N, 9.77
Experimental: C, 19.2; H, 2.96; N, 9.57

The spectroscopic features of the product in solution were the same as those of the corresponding sodium salt.

EXAMPLE 7.ter

Preparation of $[NH_4]_2[trans-RuCl_4(Me_2SO)_2](\mu$-pym), Corresponding to Formula (Ia) with $Q^+=$NH$_4^+$, L=pyrimidine (pym) and $R_1=R_2$=methyl 80 mg of $[NH_4]_2[trans-RuCl_4(Me_2SO)_2]$ (0.19 mmoles) complex was partially dissolved in 5 ml methanol. 7.7 mg (equal to 0.42 ml, 0.096 mmoles) of pyrimidine was added to the solution which was kept under stirring. 10 minutes after the addition, a clear orange-coloured solution was obtained from which the product precipitated by addition of diethyl ether. The orange precipitate was filtered in vacuum, washed with methanol and ether and vacuum-dried. Yield: 45 mg (60%). The physico-chemical features of $[NH_4]_2[trans-RuCl_4(Me_2SO)]_2(\mu$-pym) were as follows:
Physical state: orange microcrystalline solid
Raw formula: $C_8H_{24}N_4Cl_8O_2Ru_2S_2 \cdot 2H_2O$
Molecular weight: 794.21
Elemental analysis:
Theoretical: C, 12.1; H, 3.55; N, 7.05
Experimental: C, 12.4; H, 3.50; N, 6.85

The spectroscopic features of the product in solution were the same as those of the corresponding sodium salt.

EXAMPLE 8

Preparation of $[Na]_2[trans-RuCl_4(Me_2SO)]_2(\mu$-bipy), Corresponding to Formula (Ia) with $Q^+=Na^+$, L=4,4'-bipyridil (4,4'-bipy) and $R_1=R_2$=methyl The synthesis was carried out as for the corresponding compound with pyrazine. From 0.2 g of $Na[trans-RuCl_4(Me_2SO)_2]$ (47.4 mmoles) in 2 ml di $Me_2SO$ and 0.037 g of 4,4'-bipyridil (23.7 mmoles) in 5 ml of acetone, an orange microcrystalline product was obtained. Yield: 0.180 g (69.3%):

The chemico-physical features of $[Na]_2[trans-RuCl_4(Me_2SO)]_2(\mu$-4,4'-bipy) product were as follows:
Physical state: red-orange microcrystalline solid
Raw formula: $C_{14}H_{20}N_2Cl_8Na_2O_2Ru_2S_23(Me_2SO) \cdot H_2O$
Molecular weight: 1096.54
Elemental analysis:
Theoretical: C, 21.9; H, 3.68; N, 2.55
Experimental: C, 21.4; H, 3.79; N, 2.25
UV/vis spectrum in $H_2O$ ($\lambda_{max}$, nm): 459,395
$^1$H-NMR spectrum in $D_2O$ (ppm vs DSS): −16 (wide, H1, H6, H1', H6'; bipy-Ru); −14.4 (very broad, $Me_2SO$); −4.4 (broad, H3, H5, H3', H5'; bipy-Ru)
IR spectrum (selected frequencies, nujol, cm$^{-1}$): $\upsilon$ (S—O) 1096, vs; $\upsilon$ (Ru—S) 434, S; $\upsilon$ (Ru—Cl) 338, s.

EXAMPLE 9

Preparation of $[ImH]_2[trans-RuCl_4(Me_2SO)]_2$ ($\mu$-bipy), Corresponding to Formula (Ia) with $Q^+=$ImH$_+$, L=4,4'-bipyridil, $R_1=R_2$=methyl 35 mg of $[Na]_2[trans-RuCl_4(Me_2SO)]_2(\mu$-4,4'-bipy) (0.032 mmoles) was dissolved in 3 ml of $H_2O$ and 31.3 mg of solid ImHCl (0.3 mmoles) was added. The formation of dark orange crystals was observed within few hours. Yield 18 mg (60%).

The physico-chemical features of the $[ImH]_2[trans-RuCl_4(Me_2SO)]_2(\mu$-4,4'-bipy) product are as follows:
Physical state: red-orange microcrystalline solid
Raw formula: $C_{20}H_{30}N_6Cl_8O_2Ru_2S_2$
Molecular weight: 936.38
Elemental analysis:
Theoretical: C, 25.6; H, 3.23; N, 8.97
Experimental: C, 25.6; H, 3.18; N, 8.70
UV/vis spectrum in $H_2O$ ($\lambda_{max}$, nm): 459, 395
$^1$H-NMR spectrum in $D_2O$ (ppm vs DSS): −16 (broad, H1, H6, H1', H6'; bipy-Ru); −14.4 (Very broad, $Me_2SO$); −4.4 (broad, H3, H5, H3', H5'; bipy-Ru); 7.46 (ImH$^+$); 8.67 (ImH$^+$)
IR spectrum (selected frequencies, nujol, cm$^{-1}$): $\upsilon$ (S—O) 1083, vs; $\upsilon$ (Ru—S) 431, m; $\upsilon$ (Ru–Cl) 335, s.

EXAMPLE 10

Preparation of $[Na]_2[trans-RuCl_4(Me_2SO)]_2(\mu$-etbipy), Corresponding to Formula (Ia) with $Q^+$= $Na^+$, L=1,2-bis(4-pyridil)ethane (etbipy) and $R_1$=$R_2$=methyl The synthesis was carried out as for the corresponding compound with pyrazine. From 0.230 g of $Na[trans-RuCl_4(Me_2SO)_2]$ (54.5 mmoles) in 2.5 ml of $Me_2SO$ and 0.050 g of 1,2-bis(4-pyridil)ethane (27.1 mmoles) in 5 ml acetone, an orange microcrystalline product was obtained. Yield: 0.2 g (65.3%).

The physico-chemical features of $[Na]_2[trans-RuCl_4(Me_2SO)]_2(\mu$-etbipy) were as follows:
Physical state: orange microcrystalline solid
Raw formula: $C_{16}H_{24}N_2Cl_8O_2Ru_2S_2Na_2.3(Me_2SO).1H_2O$
Molecular weight: 1124.6
Elemental analysis:
Theoretical: C, 23.5; H, 3.9; N, 2.49
Experimental: C, 22.4; H, 3.7; N, 2.46
UV/vis spectrum in $H_2O(\lambda_{max}$, nm): 462, 394
$^1$H-NMR spectrum in $D_2O$ (ppm vs DSS): −14.4 (very broad, $Me_2SO$); 4.2 (broad, H3, H5, H3', H5'; etbipy-Ru); −3.8 (4, s; —$(CH_2)_2$—).
IR spectrum (selected frequencies, nujol, $cm^{-1}$): υ (S—O) 1050, vs; υ (Ru—S) 436, m; υ (Ru—Cl) 336, s

EXAMPLE 10bis

Preparation of $[ImH]_2[trans-RuCl_4(Me_2SO)]_2(\mu$-etbipy), Corresponding to Formula (Ia) with $Q^+$= $ImH^+$, L=1,2-bis(4-pyridil)ethane (etbipy) and $R_1$=$R_2$=methyl 50 mg of $[Na]_2[trans-RuCl_4(Me_2SO)]_2(\mu$-etbipy).3$(Me_2SO).1H_2O$ (0.044 mmoles) was dissolved in 10 ml of methanol; the solution is filtered on paper and then, by keeping it under stirring, 48 mg of ImHCl (0.46 mmoles) was added. An orange solid product is rapidly formed, filtered in vacuum, washed with methanol and ethyl ether and then vacuum-dried.

The physico-chemical features of $[ImH]_2[trans-RuCl_4(Me_2SO)]_2(\mu$-etbipy), were as follows:
Physical state: Solid orange
Raw formula: $C_{22}H_{34}N_6Cl_8O_2Ru_2S_2$
Molecular weight: 964.40
Elemental analysis:
Theoretical: C, 27.4; H, 3.55: N, 8.71
Experimental: C, 27.1; H, 3.56; N, 8.60

The spectroscopic features of the product in solution were the same as those of the corresponding sodium salt.

EXAMPLE 11

Preparation of mer,cis-$RuCl_3(Me_2SO)(Me_2SO)$(pyz), Corresponding to Formula (II) with L=pyrazine (pyz) and $R_1$=$R_2$=methyl 0.150 g of mer-$RuCl_3(Me_2SO)_2(Me_2O)$ (0.34 mmoles) in 3 ml of $CHCl_3$ was added to a solution of 0.082 g of pyrazine (1 mmole) in 1 ml of $CHCl_3$. The red solution got turbid and was filtered on paper. The homogeneous system obtained was kept at room temperature for one night; it was then concentrated in vacuum, with no heating, to approximately half of its volume, a few drops of ethyl ether were added and the mixture was then kept at 4° C. for a few hours. An ochre crystalline precipitate that was filtered in vacuum, washed with chloroform and ethyl ether and then vacuum-dried was obtained. In order to have precipitation to completeness of the compound, it was convenient to keep the system at 4° C. for a couple of days or else to retrieve the filtered solution and concentrate ft in vacuum so as to obtain a second fraction of product. Yield: 0.110 g (72%).

The physico-chemical features of mer,cis-$RuCl_3(Me_2SO)(Me_2SO)$(pyz) were as follows:
Physical state: ochre microcrystalline solid
Raw formula: $C_8H_{16}N_2Cl_3O_2RuS_2$
Molecular weight: 443.76
Elemental analysis:
Theoretical: C, 21.7; H, 3.63; N, 6.31
Experimental: C, 22.0; H, 3.62; N, 6.26
UV/vis Spectrum in $Me_2SO$ ($\lambda_{max}$, nm): 437, 371
$^1$H-NMR spectrum in $DMSOd_6$: (ppm vs TMS): −12.7 (very broad, $Me_2SO$); −5 (very broad, H2, H6; pyz-Ru); −0.6 (broad, H3, H5; pyz-Ru); +9.1(broad, $Me_2SO$).
IR spectrum (selected frequencies, nujol, $cm^{-1}$): υ (asymmetrical stretching pyz) 1588, m; υ (S—O) 1098; υ (S—O)912; υ (Ru—O) 488, m; υ(Ru—S) 422, m; υ(Ru—Cl) 353, 337, s.

EXAMPLE 12

Preparation of $[NH_4][trans-RuCl_4(Me_2SO)]_2(\mu$-pyz)[mer,cis-$RuCl_3(Me_2SO)(Me_2SO)$], Corresponding to Formula (Ib) with $Q^+$=$NH_4^+$, L=pyrazine (pyz) and $R_1$=$R_2$=methyl 53 mg of mer,cis-$RuCl_3(Me_2SO)(Me_2SO)$(pyz) (0.12 mmoles) in 5 ml of $CHCl_3$ was added to a solution containing 63 mg of $[NH_4][trans-RuCl_4(Me_2SO)_2]$ (0.15 mmoles) in 7 ml of methanol. Within a few hours, an orange precipitate was formed, which was then filtered, washed with cold methanol, chloroform and ethyl ether. Yield: 60%.

The physico-chemical features of the $[NH_4][trans-RuCl_4(Me_2SO)]_2(\mu$-Pyz)[mer,cis-$RuCl_3(Me_2SO)(Me_2SO)$] were as follows:
Physical state: Solid yellow compound
Raw formula: $C_{10}H_{26}N_3Cl_7O_3Ru_2S_3.CH_3OH.½CHCl_3$
Molecular weight: 874.55
Elemental analysis:
Theoretical: C, 15.8; H, 3.51; N, 4.80
Experimental: C, 15.9; H, 3.58; N, 4.83
UV/vis Spectrum in $Me_2SO$ ($\lambda_{max}$, nm): 389
$^1$H-NMR spectrum in $D_2O$: (ppm vs TMS): −14.4(very wide, $Me_2SO$); 9.8 (wide, $Me_2SO$)
IR spectrum (selected frequencies, nujol, $cm^{-1}$): υ (S—O) 1089, vs; υ (S—O) 912, vs; υ (S—O) 912, vs; υ (Ru—O) 494, m; υ (Ru—S) 434, m; υ (Ru—Cl) 335, vs.

EXAMPLE 13

Preparation of [mer,cis-$RuCl_3(Me_2SO)(Me_2SO)(\mu$-pyz)], Corresponding to Formula (Ic) with L=pyrazine (pyz) and $R_1$=R=methyl 0.009 g of pyrazine (11.2 mmoles) dissolved in 5 ml of $CHCl_3$ was added to 0.100 g of mer-$RuCl_3(Me_2SO)_2(Me_2SO)$ dissolved in 5 ml of $CHCl_3$ and the red solution was kept under magnetic stirring at room temperature. The system got turbid because of the formation of the reaction product which was then reacted under stirring for one night. The yellow precipitate was finally filtered, washed with $CHCl_3$ and ether and vacuum-dried. Yield: 0.065 g (71%).

The physico-chemical features of [mer,cis-$RuCl_3(Me_2SO)(Me_2SO)]_2(\mu$-pyz) product were as follows:
Physical state: Solid yellow compound Raw formula: $C_{12}H_{28}N_2Cl_6O_4Ru_2S_4$
Molecular weight: 807.4
Elemental analysis:
Theoretical: C, 17.8; H, 3.50; N, 3.47
Experimental: C, 16.8; H, 3.00; N, 3.08
UV/vis spectrum in $Me_2SO$ ($\lambda_{max}$, nm): 439, 378
$^1$H-NMR spectrum in $DMSOd_6$: (ppm vs TMS): 13.2 ($Me_2SO$); +8.3 ($Me_2SO$)
IR spectrum (selected frequencies, nujol, cm$^-$): υ (S—O) 1106, vs; υ (S—O) 893, vs; υ (Ru—O) 494, vs; υ (Ru—S) 426, m; υ (Ru—Cl) 341, vs.

Stability Tests of the Compounds

EXAMPLE 14

Stability in acqueous solutions

The stability of the complexes obtained was tested in aqueous and physiological solutions according to the time trend of the absorbance in UV/vis spectrum. The maximum absorbance at 390 nm was selected and the decrease of the absorbance percentage with time was measured.

The experiments were carried out at the temperature of 25.0° C. in aqueous solutions (distilled water) and physiological solution (pH=7.4, 0.1 M phosphate buffer, 0.1M NaCl) of the compound at a concentration of $1 \times 10^4$ M for the duration of 140 minutes.

Stability testing of the following compounds was performed:

$[Na]_2[trans\text{-}RuCl_4(Me_2SO)]_2(\mu\text{-pyz})$ (ex.4)
$[Na]_2[trans\text{-}RuCl_4(Me_2SO)]_2(\mu\text{-pym})$ (ex.7)
$[Na]_2[trans\text{-}RuCl_4(Me_2SO)]_2(\mu\text{-4,4'-bipy})$ (ex.8)
$[Na]_2[trans\text{-}RuCl_4(Me_2SO)]_2(\mu\text{-etbipy})$ (ex.10)

This stability test was carried out also on a known ruthenium complex of formula [trans-RuCl$_4$(Me$_2$SO)(Im)][ImH] (WO98/00431).

Figure 1A:
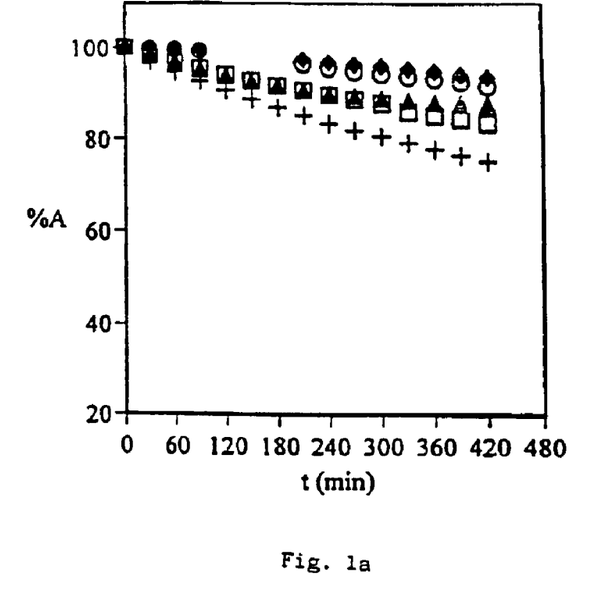
Figure 1B:
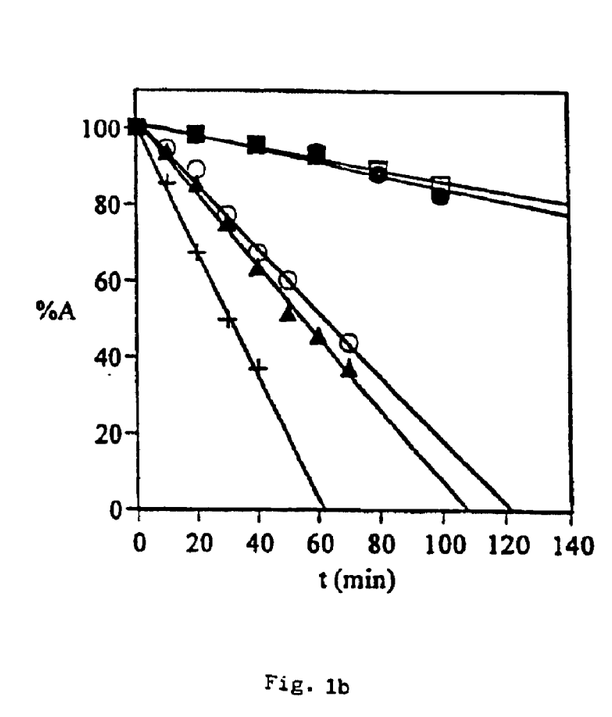

FIGS. 1a and 1b show a decrease in the absorbance percentage with time, which reveals the hydrolysis of the complexes. The absorbance decrease was reduced when the complexes were dissolved in water while it was more marked when this stability test was carried out in physiological solution.

Generally, the new complexes in solution were stabler than the known complex. In the physiological solution too, where hydrolysis of all the compounds is faster than in water, the new series of ruthenium derivatives exhibited ascertained advantages in terms of stability with respect to the known ruthenium complexes.

Biological Activity Tests

EXAMPLE 15

In vivo tests of the activity of the compounds according to the present invention in mice affected from MCa mammary carcinoma: prevention activity in the formation of lung metastases.

Five groups of CBA kin female mice weighing 23±3 g were inoculated with $10^{-6}$ viable cells (as determined by the Trypan blue exclusion) of MCa mammary carcinoma in 0.05 ml Dulbecco's pH 7.4 buffered calcium and magnesium-free solution (PBS), by intramuscular injection with a sterile insulin syringe. The tumour cells were derived from donors of the same strain, injected with the same tumour cells, following the same procedures 2 weeks before. The suspension of tumour cells was prepared in PBS by mechanically mincing the tumour mass obtained from donor mice, and further removing tissue debris and cells by, respectively, filtration through a double layer of sterile gauze and centrifugation at 250× g for 10 minutes. Kin animals were obtained from a colony from Chester Beatthy from London (UK) which were grown in the University of Trieste animal house accordingly to the procedures accepted for the rearing of kin animals. The MCa mammary carcinoma tumour cell-line derived from a stock, stored in liquid nitrogen, of tumour cells obtained originally from Rudjer Boskovic Institute of Zagreb (HR).

From day 11 to day 16, after tumour cells implantation, five mice groups were treated intraperitoneally with a sterile insulin syringe, respectively with:

Group 1 Control (10 animals): 10 ml/kg of body weight/day of sterile and pyrogen-free physiological solution;

Group 2 (two subgroups a,b of five animals each): 7.5 (a), 15 (b) mg/kg of body weight/day of the compound prepared as described in Example 4 in sterile and pyrogen-free physiological solution;

Group 3 (2 subgroups c,d of five animals each): 15 (c), 30 (d) mg/kg of body weight/day of the compound prepared as described in Example 7 in sterile and pyrogen-free physiological solution;

Group 4 (2 subgroups e,f of 5 animals each): 25 (e), 50 (f) mg/kg of body weight/day of the compound prepared as described in Example 8 in sterile and pyrogen-free physiological solution;

Group 5 (2 subgroups g,h of 5 animals each): 12.5 (g), 25 (h) mg/kg of body weight/day of the compound prepared as described in Example 10 in sterile and pyrogen-free physiological solution.

The administered dosages were either approximated to $LD_{0.1}$, or to half of it or to a quarter of it, as calculated separately in animals of the same strain and gender and with the same body weight, for an intraperitoneal treatment lasting 6 consecutive days, according to the method of Lichtfield and Wilcoxon, and with an observation time of 10 days since the last dose.

On day 17 since tumour cells implantation, the primary tumour was surgically removed, after general anesthesia of the animals by intraperitoneal injection of 125 mg/kg of Ketamine.

On day 29 since tumour cells implantation, the mice were sacrificed by cervical dislocation for the evaluation of lung metastases. The lungs were abducted from the animals immediately after sacrifice, divided in single lobes which then examined immediately with a low-magnification microscope equipped with a graduated ocular-grid for the measurement of the size of the metastases in which the a and b orthogonal axes (a≦b) were identified. Metastases were classified by size and the metastatic tumour weight for each animal was calculated as the sum of each single metastasis weight, each of them considered as a rotation solid developed around the above mentioned axes and calculated according to the formula $(\pi/6) \cdot a^2 \cdot b$. The experimental data obtained were then processed by appropriate statistical tests.

The results are reported in Table 1, where the body weight variation from the beginning (day 11) to the end (day 16) of the treatment with respect to the untreated controls, and the number and weight of lung metastases obtained in groups of animals treated with the compounds of the present invention with respect to the group of controls treated with sterile and pyrogen-free physiological solution, are shown.

TABLE 1

Effects of pre-surgical treatment with the compounds described in Examples 4, 7, 8, 10 on the formation of lung metastases in mice affected by MCa mammary carcinoma.

| Treatment | Dose mg/kg/die | Body weight % var | Lung metastases Number mean | min-max | % T/C* | weight (mg) mean | min-max | % T/C |
|---|---|---|---|---|---|---|---|---|
| Group 1   | 0    | —    | 52.0 | 3–77   | 100 | 82.4 | 0.2–251 | 100 |
| Group 2-a | 7.5  | −4.6 | 14.0 | 9–40   | 27  | 8    | 1.4–158 | 10  |
| Group 2-b | 15   | −3.3 | 2.0  | 1–60   | 4   | 0.2  | 0.1–95  | 0   |
| Group 3-c | 15   | −1.4 | 5.0  | 4–20   | 10  | 1.7  | 1–60    | 2   |
| Group 3-d | 30   | −2.7 | 3.0  | 2–24   | 6   | 0.8  | 0.3–16  | 1   |
| Group 4-e | 25   | −3.4 | 111  | 49–142 | 213 | 119  | 58–169  | 144 |
| Group 4-f | 50   | −1.7 | 8.0  | 1–39   | 15  | 3.1  | 0.4–25  | 4   |
| Group 5-g | 12.5 | −2.8 | 8.0  | 4–45   | 15  | 4.6  | 0.7–16  | 6   |
| Group 5-h | 25   | −1.1 | 13.0 | 0–29   | 25  | 1.2  | 0–18    | 1   |

*% T/C: Treated/Control

The data reported in Table 1, show that all four compounds are well tolerated by the animals during treatment, as can be seen by the scarce statistical relevance of the body weight variation with respect to the controls.

None of the compounds examined, at none of the tested dosage, show a variation in the growth of the primary tumour. However, among the compounds tested, those described in Examples 4, 7 and 10 in particular, caused a marked reduction in the number and an even more marked reduction in the weight of lung metastases at two dose levels. In some cases the reduction of the average value of metastases is reduced to less than 5% of the controls.

EXAMPLE 16

In vivo testing of the activity of the compounds according to the present invention in mice affected by MCa mammary carcinoma: inhibition activity of lung metastases at an advanced stage of growth.

Five groups of CBA kin female mice weighing 23±3 g were inoculated with $10^{-6}$ viable MCa mammary carcinoma cells (as determined by trypan blue exclusion) in 0.05 ml Dulbecco's pH 7.4 buffered calcium- and magnesium-free solution (PBS) by intramuscular injection with a sterile insulin syringe. The tumour cells were derived from donors of the same strain injected with the same tumour cells and with the same procedures 2 weeks before. The suspension of tumour cells was prepared in PBS by mechanical mincing of the tumour mass obtained from donor mice, and further removal of tissue debris and cells was obtained, respectively, by filtration through a double layer of sterile gauze and centrifugation at 250× g for 10 minutes. Kin animals were obtained from a colony from Chester Beatthy from London (UK) and were grown in the University of Trieste animal house accordingly to the procedures accepted for the rearing of kin animals. The MCa mammary carcinoma tumour cell-line was derived from a stock, stored in liquid nitrogen, of tumour cells originally obtained from Rudjer Boskovic Institute of Zagreb (HR).

On day 14 since tumour cells implantation, the primary tumour was surgically removed, after general anesthesia of the animals by intraperitoneal injection of 125 mg/kg of Ketamine.

From day 15 to day 20 after tumour cells implantation, the five mice groups were treated, intraperitoneally with a sterile insulin syringe, respectively with:

Group 1 Control (7 animals): 10 ml/kg of body weight/day of sterile and pyrogen-free physiological solution;

Group 2 (7 animals): 28 mg/kg of body weight/day of the compound as prepared in Example 4 in sterile and pyrogen-free physiological solution;

Group 3 (7 animals): 28 mg/kg of body weight/day of the compound as prepared in Example 7 in sterile and pyrogen-free physiological solution;

Group 4 (7 animals): 51 mg/kg of body weight/day of the compound as prepared in Example 8 in sterile and pyrogen-free physiological solution;

Group 5 (7 animals): 52 mg/kg of body weight/day of the compound as prepared in Example 10 in sterile and pyrogen-free physiological solution.

The dosages corresponding to the $LD_{0.05}$, calculated separately in animals of the same strain and gender and having the same body weight, was administered intraperitoneally for 6 consecutive days, according to the method of Lichtfield and Wilcoxon, and with an observation time of 10 days since last dose.

On day 28 since tumour cells implantation, the mice were sacrificed by cervical dislocation for the evaluation of lung metastases. The lungs were abducted from the animals immediately after sacrifice, divided in single lobes that were soon examined with a low-magnification microscope equipped with a graduated ocular-grid for the measurement of metastases size, where the orthogonal axes a and b (a≦b) were identified. The metastases were then classified by size and the metastatic tumour weight for each animal was calculated as the sum of each single metastasis weight, each of them considered as a rotation solid developed around the above mentioned axes according to the formula $(\pi/6) \cdot a^2 \cdot b$. The experimental data obtained were then processed by appropriate statistical tests.

The results are reported in Table 2, where the number and weight of lung metastases obtained in groups of animals treated with the compounds of the present invention with respect to the group of controls treated with sterile and pyrogen-free physiological solution, are shown.

TABLE 2

Effects of the post-surgical treatment with the compounds described in Examples 4, 7, 8, 10 on the spontaneous lung metastases of MCa mammary carcinoma in CBA mice.

| Treatment | Lung metastases Number | % T/C* | Weight (mg) | % T/C |
|---|---|---|---|---|
| Group 1 | 52.0 ± 9.7  | 100 | 244 ± 43 | 100 |
| Group 2 | 41.4 ± 8.0  | 80  | 96 ± 20  | 39  |
| Group 3 | 40.4 ± 7.4  | 78  | 107 ± 31 | 44  |
| Group 4 | 20.6 ± 7.3  | 40  | 76 ± 31  | 31  |
| Group 5 | 27.8 ± 7.8  | 53  | 71 ± 20  | 29  |

*% T/C: Treated/Control

The data reported in Table 2 confirm the activity of the compounds of Examples 4, 7, 8, 10 on lung metastases of MCa mammary carcinoma. All four compounds and specifically the compounds in Examples 8 and 10 were able to reduce significantly the growth of the lung metastases of this tumour.

The ruthenium dimers of Examples 4, 7, 8, 10 tested for their pharmacological activity in the MCa mammary carcinoma model of the CBA mouse, showed the ability to act selectively on lung metastases. Such ability was not correlated to analogous effects on the growth of the primary tumour.

EXAMPLE 17

In vitro cytotoxicity of complexes of the present invention on murine TS/A adenocarcinoma cells.

$4 \times 10^3$ murine TS/A adenocarcinoma cells resuspended in 200 µl RPMI-1640 medium supplemented with 10% FCS (fetal calf serum), 2 mM glutamine and 50 µg/ml gentamicin sulphate, were seeded in a 96-wells plate. After 24 hours incubation at 37° C., in 5% $CO_2$, the complexes as described in example 4 (A), in example 7 (B), in example 8 (C) and in example 10 (D), each solubilised in RPMI-1640 medium supplemented with 5% FCS, 2 mM glutamine and 50 µg/ml gentamicin sulphate, were added to the cells, each at a final concentration of $10^{-4}$, $10^{-5}$ and $10^{-6}$ M. Cell viability tests were performed after 24, 48 and 72 hours of exposure to the compounds by assessing both the effect on protein synthesis and on mitochondrial activity by means of colorimetric assays, respectively the solphorodamine B test (SRB) and the MTT analysis. Each value (optical density) is the average percentage ±S.E. versus the untreated controls.

Values such as *p<0.05, **p<0.01 indicate average values statistically different from the controls. Analysis of Variance and Dunnet test were used in the comparison analysis.

The results are reported in Table 3, wherein both the effect on protein synthesis (SRB) and the mitochondrial activity (MTT) are reported for each complexes tested at different dosages after different exposure time.

Under this condition the complexes did not cause any cytotoxic effect. Although a certain antiproliferative activity was observed on cells treated with the complexes of examples 4 and 8 for long period of time, this effect appeared to be scarce and reversible. In fact, the cells recovered their original proliferative ability after the first 24 hours of exposure, as can be inferred from th data related to the 48 and 72 hours exposure time.

These data show that the antimetastatic activity of the complexes of the present is invention could not be ascribed only to an in vitro cytotoxic effect.

What is claimed is:

1. Ruthenium complexes of formula (I)

wherein:

L represents an heterocylic ligand containing at least two nitrogen heteroatoms wherein the electronic doublets of said nitrogen atoms are involved in the bond with two ruthenium atoms, X, Y and Z independent from one another represent: $Cl^-$, $OS(R_1R_2)$, $R_1$ and $R_2$, independent from one another, either represent: $C_1$–$C_6$ alkyl, cycloalkyl, phenyl and aryl, or $R_1$ and $R_2$ together with the sulfur (S) atom, form a 5–7 membered ring, m is an integer ranging from 0 to 2, and when m is different from 0, the negative charge of the compound of formula (I) is neutralized by a Q counterion suitable for pharmaceutical use.

TABLE 3

In vitro cytotoxicity of complexes A, B, C, D (described respectively in examples 4, 7, 8, 10) tested on murine adenocarcinoma cells TS/A.

| Complex-dose (M) | Exposure time (h) | | | | | |
|---|---|---|---|---|---|---|
| | SRB | | | MTT | | |
| | 24 | 48 | 72 | 24 | 48 | 72 |
| Controls | 100 ± 6 | 100 ± 1 | 100 ± 2 | 100 ± 10 | 100 ± 5 | 100 ± 4 |
| A-$10^{-6}$ | 112 ± 3 | 102 ± 5 | 107 ± 2 | 105 ± 10 | 101 ± 9 | 89 ± 2 |
| A-$10^{-5}$ | 99 ± 5 | 95 ± 1 | 95 ± 2 | 100 ± 10 | 108 ± 12 | 93 ± 4 |
| A-$10^{-4}$ | 32 ± 1** | 51 ± 2** | 66 ± 2** | 34 ± 1** | 50 ± 7** | 59 ± 1** |
| B-$10^{-6}$ | 101 ± 9 | 100 ± 3 | 95 ± 7 | 110 ± 2 | 110 ± 13 | 104 ± 8 |
| B-$10^{-5}$ | 95 ± 9 | 108 ± 5 | 100 ± 1 | 117 ± 1 | 104 ± 9 | 93 ± 9 |
| B-$10^{-4}$ | 58 ± 2** | 73 ± 8* | 61 ± 2** | 90 ± 10 | 71 ± 12* | 60 ± 1** |
| C-$10^{-6}$ | 77 ± 6 | 92 ± 8 | 95 ± 2 | 91 ± 7 | 103 ± 9 | 93 ± 5 |
| C-$10^{-5}$ | 102 ± 9 | 86 ± 9 | 88 ± 7 | 129 ± 9 | 91 ± 3 | 90 ± 2 |
| C-$10^{-4}$ | 16 ± 1** | 49 ± 6** | 78 ± 5** | 33 ± 5** | 52 ± 9** | 68 ± 4** |
| D-$10^{-6}$ | 102 ± 9 | 81 ± 5 | 93 ± 5 | 114 ± 7 | 109 ± 4 | 88 ± 4 |
| D-$10^{-5}$ | 81 ± 8 | 94 ± 3 | 95 ± 1 | 97 ± 12 | 93 ± 2 | 84 ± 5 |
| D-$10^{-4}$ | 47 ± 2** | 62 ± 14** | 73 ± 2** | 76 ± 9 | 65 ± 4** | 76 ± 4** |

The data reported in table 3 show that the dimeric complexes of the invention show scarce antiproliferative effect when they were tested in vitro on tumour cells also when high doses are applied. In fact, the inhibition of cell proliferation was not evident at doses lower than $10^{-4}$ M.

2. Complexes according to claim 1, where the two nitrogen heteroatoms bound to the two ruthenium atoms of formula (I) are contained onto the same heterocylic ring.

3. Complexes according to claim 1, wherein the two nitrogen heteroatoms bound to the two ruthenium atoms of formula (I) are contained onto two separate nitrogen heterocylic rings, A' and A", where said L ligand takes a A'—K—A" structure and K represents: —COO—, —O—, —(CH$_2$)$_n$—, —(CH=CH)$_n$—, -(aryl)$_n$-, -heterocycle)$_n$-, —CH=CH—Phe—CH=CH—, —(C≡C)$_n$, where n ranges from 0 to 4.

4. Complexes according to claim 3, wherein said A'—K—A" structure represents one of the structures selected from the group consisting of:
4,4'-bipyridil: (A=pyridine, K=—(CH$_2$)$_n$—, n=0),
bis-imidazole: (A=imidazole, K=—(CH$_2$)$_n$—, n=0),
1,2-bis(4-pyridil)ethane: (A=pyridine, K=—(CH$_2$)$_n$—, n=2),
2-bis(4-pyridil)propane: (A=pyridine, K=—(CH$_2$)$_n$—, n=3, and
trans-1,2-bis(4-pyridil)ethylene: (A=pyridine, K=—(CH=CH)$_n$—, n=1).

5. Complexes according to any one of claims 1, 2, 3, or 4, where either R$_1$ and R$_2$, independent one another, represent methyl or ethyl, or R$_1$ and R$_2$, together with the S atom, form a 5-membered ring (tetramethylensulfoxide).

6. Complexes according to any one of claims 1, 2, 3, or 4, where the Q counterion is selected from the group consisting of: an alkaline or an alkaline-earth metal cation, and a cation of formula NHR$_3$R$_4$R$_5^+$ where R$_3$, R$_4$, R$_5$ are identical or different from one another and are selected from the group consisting of: H, C$_1$–C$_6$ alkyl, C$_3$–C$_7$ cycloalkyl, phenyl and aryl, or NHR$_3$R$_4$R$_5^+$ is 5–7 membered nitrogen heterocycle optionally fused with a benzyl group.

7. Complexes according to any one of claims 1, 2, 3, or, 4, where Q is selected from the group consisting of Na$^+$, K$^+$, NH$_4^+$, NEt$_4^+$ (ethylammonium), and ImH$^+$ (imidazolium).

8. Complexes according to any one of claims 1, 2, 3, or 4 in the form of symmetrical dianionic Ru(III) dimers wherein X=Y=Z=Cl$^-$, and m=2.

9. Complexes according to any one of claims 1, 2, 3, or 4, in the form of asymmetrical mono-anionic dimers of Ru(III) wherein X=Z=Cl$^-$, Y=OSR$_1$R$_2$ and m=1.

10. Complexes according to any one of claims 1, 2, 3, or 4, in the form of symmetrical neutral Ru(III) dimers wherein X=Y=OSR$_1$R$_2$, Z=Cl$^-$ and m=0.

11. Process for the preparation of the complexes of formula (I) as described in claim 1, characterised by the fact that a precursor having formula (III), (III)

wherein:
W is selected from the group consisting of: Cl$^-$ and OSR$_1$R$_2$,
R$_1$ and R$_2$, independent from one another, either represent: C$_1$–C$_6$ alkyl, C$_3$–C$_7$ cycloalkyl, phenyl and aryl, or R$_1$ and R$_2$ together with the sulfur (S) atom, form a 5–7 membered heterocyclic ring,
m is an integer ranging from 0 to 2,
and when m is different from 0, the negative charge of the compound of formula (III) is neutralized by a Q counterion suitable for pharmaceutical use,
is reacted with a ligand L as defined in claim 1, and optionally with a second precursor of formula (III) as defined above, wherein W is different from the one in the first precursor.

12. Process according to claim 11 for the preparation of symmetric dianionic dimers of formula (Ia) wherein the precursor of formula (III) composed of Q[trans-RuCl$_4$(R$_1$R$_2$SO)$_2$] (Q$^+$=Na$^+$, K$^+$, NH$_4^+$, ImH$^+$) is reacted with the ligand L according to the general scheme reported hereunder:

(Ia)

13. Process according to claim 11 for the preparation of asymmetric monoanionic Ru(III) dimers of formula (Ib), wherein the precursor of formula (III) composed of [mer-RuCl$_3$(Me$_2$SO)$_3$] is reacted with the ligand L, according to the scheme reported hereunder:

(II)

and wherein the compound of formula (II) is reacted with the second precursor of formula (III), Q[trans-RuCl$_4$(R$_1$R$_2$SO)$_2$] according to the scheme reported hereunder:

(Ib)

14. Process according to claim 11 for the preparation of symmetric neutral dimers of formula (Ic), wherein the precursor of formula (III), [mer-RuCl$_3$(R$_1$R$_2$SO)$_3$] is reacted with the ligand L, according to the scheme reported hereunder:

(Ic)

15. Pharmaceutical composition containing one or more ruthenium complexes of formula (I)

wherein:

L represents an heterocylic ligand containing at least two nitrogen heteroatoms wherein the electronic doublets of said nitrogen atoms are involved in the bond with two ruthenium atoms, X, Y and Z independent from one another represent: Cl⁻, OS(R₁R₂), R₁ and R₂, independent from one another, either represent: $C_1$–$C_6$ alkyl cycloalkyl, phenyl and aryl, or R₁ and R₂ together with the sulfur (S) atom, form a 5–7 membered ring, m is an integer ranging from 0 to 2, and when m is different from 0, the negative charge of the compound of formula (I) is neutralized by a Q counterion suitable for pharmaceutical use, in combination with pharmaceutically acceptable excipients and diluents.

16. Pharmaceutical composition according to claim 15, suitable for oral, topical, transdermal and parenteral administration.

17. Pharmaceutical composition according to any one of claims 15–16 the form of topical inserts, gel, cream, granules, powder, tablets, capsules, pills, solutions or suspensions, freeze-dried solid.

18. Pharmaceutical composition according to any one of claims 15–16 suitable for a controlled release of the active compound.

19. Method for the treatment of metastases and tumours in a human or animal in need thereof comprising, administrating to said patient of one or more complexes of formula (I)

wherein:

L represents an heterocyclic ligand containing at least two nitrogen heteroatoms wherein the electronic doublets of said nitrogen atoms are involved in the bond with two ruthenium atoms, X, Y, and Z independent from one another represent Cl⁻, OS(R₁R₂), R₁ and R₂, independent from one another, either represent: $C_1$–$C_6$ alkyl, cycloalkyl, phenyl and aryl, or R₁ and R₂ together with the sulfur atom, form a 5–7 membered ring, m is an integer ranging from 0 to 2, and when m is different from 0, the negative charge of the compound of formula (I) is neutralized by a Q counterion suitable for pharmaceutical use, for the preparation of a medicament for the prevention and treatment of metastases and tumours in the human or animal in need thereof.

20. The method according to claim 19, wherein said drug with antimetastatic and antitumour activity is used in the treatment of metastasizing solid tumours.

21. The method according to claim 20, wherein said metastasizing solid tumours are selected from the group consisting of: carcinomas of the digestive tract, mammary carcinomas, and the lung carcinomas.

22. Complexes according to claim 1, wherein said heterocyclic ligand L contains one or more heterocycles selected from the group consisting of imidazole, pyrazole, pyrazine, and pyrimidine.

23. Complexes according to claim 1, wherein said heterocyclic ligand L contains two or more heterocycles selected from the group consisting of pyrrole, pyridine, quinoline, isoquinoline, and carbazole.

* * * * *